United States Patent [19]

Halpern et al.

[11] Patent Number: 4,551,527

[45] Date of Patent: Nov. 5, 1985

[54] SALTS OF 5,5-BIS-(BROMOMETHYL)-2-HYDROXY-2-OXO-1,3,2-DIOXAPHOSPHORINANE AND PROCESS FOR PREPARING SAME

[75] Inventors: Yuval Halpern, Skokie; Donna Mott, Des Plaines, both of Ill.

[73] Assignee: Borg-Warner Chemicals, Inc., Parkersburg, W. Va.

[21] Appl. No.: 279,636

[22] Filed: Jul. 2, 1981

[51] Int. Cl.$^4$ ............................ C07F 9/65; C07F 9/15
[52] U.S. Cl. ................... 544/214; 260/937; 260/987; 524/118; 556/24; 556/174
[58] Field of Search .............. 260/987, 937, 448 R, 260/924, 925, 429.9; 544/214; 541/180

[56] References Cited

U.S. PATENT DOCUMENTS

| | | | |
|---|---|---|---|
| 2,202,124 | 5/1940 | Tattersall | 260/925 |
| 3,159,664 | 12/1964 | Bartlett | 260/987 X |
| 3,412,118 | 11/1968 | Kujawa et al. | 260/448 R |
| 3,825,629 | 7/1974 | Hofer et al. | 260/448 R |
| 3,875,264 | 4/1974 | Hofer et al. | 260/448 R |
| 4,143,101 | 3/1979 | Mayherhoefer et al. | 260/927 R |
| 4,201,705 | 5/1980 | Halpern et al. | 260/927 R |
| 4,233,253 | 11/1980 | Hoff et al. | 260/987 |
| 4,365,033 | 12/1982 | Halpern et al. | 260/937 |

OTHER PUBLICATIONS

Kosolapoff, "Organophosphorus Compounds", Wiley, New York (1950) pp. 279–281.
Ukita et al., "Pharm. Bull." (Tokyo), 5, (1957) pp. 121–126.
Eidebenz et al., "Iodine–Containing Aliphatic Phosphoric Acid Esters", *Arch. Pharm.*, 280 (1942), pp. 227–231.
Edmundson, "Tetrahedron", 29(9), (1965) pp. 2379–2387.

*Primary Examiner*—Anton H. Sutto
*Attorney, Agent, or Firm*—Richard J. Schlott

[57] ABSTRACT

A process for preparing polyvalent metal and amine salts of the indicated phosphorinane (an acid). The salts are isolated as such and are effective, in small proportions, to impart flame-retardant properties to polymers, especially to polypropylene and to styrenic polymers such as polystyrene, ABS and MBS.

13 Claims, No Drawings

SALTS OF 5,5-BIS-(BROMOMETHYL)-2-HYDROXY-2-OXO-1,3,2-DIOXAPHOSPHORINANE AND PROCESS FOR PREPARING SAME

This invention relates as indicated to a process for preparing certain salts of phosphorus- and bromine-containing acids. More particularly, it relates to the preparation of polyvalent metal salts and amine salts. The salts thus prepared are useful as flame-retardants in polymer compositions. They are also useful as extreme pressure additives in gear lubricating compositions.

BACKGROUND OF THE INVENTION

Polymers vary widely in their resistance to burning. Some, such as the polyolefins, polystyrene, polyalkyl acrylates and methacrylates, and the like, burn readily. Polytetrafluoroethylene, polyvinylidene chloride and polyvinyl chloride, on the other hand, have a rather high resistance to burning. In any event, it obviously is highly desirable that, for certain applications, a polymer should have a high degree of flame retardance so that it will meet the requirements of various building codes or that it will meet safety standards imposed on toys, carpeting, drapery materials, automotive applications, etc.

The treatment of these more flammable polymers to increase their resistance to burning is well known; such treatment generally has involved the incorporation in the polymer composition of substantial proportions of antimony oxide, halogenated paraffins, halogenated hydrocarbons and low molecular weight phosphate esters. Ordinarily, though, the effective use of these and other additives has required their presence in such high concentrations as to adversely affect the desirable properties of the polymer. Thus, such desirable properties as hardness, clarity, strength, elasticity, etc., are diminished significantly by the presence of large amounts of a flame-retardant chemical.

The formulator's goal, in preparing a flame-retardant polymer composition, is to add just enough of the flame retardant compound so as to provide the desired degree of flame retardance, but no more than this minimum amount, so as to the polymer. Frequently, it is not possible to select a flame-retardant which will meet these requirements satisfactorily.

The formation of ammonium salts of phosphoric acid resulting from the reaction of $CH_3CH(OH)CH_2OH$ and $(CH_2CHOH)_2$ with phosphorus oxychloride is shown in "Organic Phosphates," Ukita et al., Pharm. Bull (Tokyo) 5, 121–6 (1957). The salts are said to be insoluble in isopropyl alcohol. They were prepared for purposes of comparison with cyclic nucleotides. There is no suggestion of their utility as flame-retardants.

The preparation of the calcium salt of pentaerythritoldiiodohydrin phosphoric acid is shown in "Iodine-Containing Aliphatic Phosphoric Acid Esters," Eidebenz et al., Arch. Pharm. 280, 227–31 (1942).

The ammonium salt of 5,5-dimethyl-2-hydroxy-2-oxo-1,3,2-dioxaphosphorinane is shown in "Cyclic Organophosphorus Compounds-III," Edmundson, Tetrahedron, 21(9), 2379–87 (1965). Also, the preparation of the potassium salt is shown by neutralization of the acid with aqueous potassium bicarbonate and evaporation to dryness.

SUMMARY OF THE INVENTION

The process of the present invention makes available certin salts of 5,5-bis-(bromomethyl)-2-hydroxy-2-oxo-1,3,2-dioxaphosphorinane by reacting said acid or the acid chloride thereof with a water-soluble metal salt, basic metal compound or amine, to form the corresponding salt, and isolating said salt from the process mixture. As noted earlier, the salts prepared in this manner are effective flame-retardants in polymer compositions.

DETAILED DESCRIPTION OF THE INVENTION

Although the acid used in the above process is itself an effective flame-retardant additive in a wide variety of polymer compositions, its use is limited by the fact that polymer compositions containing such acid are susceptible to development of color at elevated temperatures. The metal and amine salts prepared by the process herein to not cause any substantial color in polymer compositions under those conditions and, for this reason, are more desirable.

The water-soluble metal salts or basic metal compounds contemplated above include the chlorides, bromides, nitrates, sulfates, oxides, hydroxides, carbonates, bicarbonates and lower (1–4 carbon atoms) alkoxides of sodium, potassium, calcium, magnesium, barium, strontium, antimony, silver, copper, nickel, iron, cobalt, zinc, iron, manganese, molybdenum, chromium, titanium, zirconium, cadmium, aluminum, bismuth, lead, tin, and vanadium. Aluminum and calcium are preferred.

The acid reactant is soluble in water and the process ordinarily is carried out conveniently in the presence of sufficient water to afford a solution of the reactants. At least stoichiometric quantities of the metal reactant or amine are used. Generally, more than the stoichiometric amount is used. Fortunately, the salts are less soluble in water than the acid itself, and this permits a relatively simple means of isolating the salt product. Generally, the process is carried out at an elevated temperature, i.e., between about 60° C. and 100° C., then on cooling, the salt product crystallizes from solution and is collected on a filter.

The process is illustrated by the following examples, showing the preparation of various salts (as indicated) of 5,5-bis-(bromomethyl)-2-chloro-2-oxo-1,3,2-dioxaphosphorinane.

EXAMPLE 1

(Aluminum Salt)

To a solution of 64.8 g. (0.2 mol) of 5,5-bis-(bromomethyl)-2-hydroxy-2-oxo-1,3,2-dioxaphosphorinane in 250 ml. of water (at 90° C.) there is added a hot solution (90° C.) of 144.9 g. (0.6 mol) of aluminum chloride hexahydrate in 100 ml. of water. The addition is made slowly, with stirring and when all is added the resulting mixture is cooled slowly to room temperature and filtered. The solid is washed with 50 ml. of cold water and dried at 100° C. under vacuum to constant weight. Yield: 52.3 g. (79% of the theory). Elemental analysis correspond to $C_{15}H_{24}Br_6O_{12}P_3Al$.

EXAMPLE 2

(Calcium Salt)

To a solution of 64.8 g. (0.2 mol) of 5,5-bis-(bromomethyl)-2-hydroxy-2-oxo-1,3,2-dioxaphosphorinane in 250 ml. of water (at 90° C.) there is added a hot solution (90° C.) of 131.4 g. (0.6 mol) of calcium chloride hexahydrate in 100 ml. of water. The solutions are mixed as above resulting in the formation of 63.7 g. (99% of the theory) of the calcium salt.

EXAMPLE 3

(Melamine Salt)

To a mixture of 6.85 g. (0.02 mol) of 5,5-bis-(bromomethyl)-2-chloro-2-oxo-1,3,2-dioxaphosphorinane and 2.52 g. (0.02 mol) of melamine there is added 20 ml. of water and the resulting mixture is stirred at 100° C. for 15 minutes, then cooled slowly to room temperature and then in an ice bath. Filtration yields 8.43 g. (92% of the theory) of a white powder, identified by elemental analysis as the melamine salt ($C_8H_{15}Br_2N_6O_4P$).

The preferred salts are the alkaline earth metal, aluminum and melamine salts. Their preferred method of preparation involves the use of the corresponding metal halide or melamine, as the case may be.

The polymers especially susceptible to improvement, with respect to flame-retardant properties imparted by the presence of small proportions of these additives, include principally polypropylene and styrene polymers. The additives are effective when used alone, or in combination with a synergist such as antimony trioxide.

The metal salt additives herein should ordinarily be used in concentrations ranging from about 20 pph (parts per hundred parts of resin) to about 32 pph. When desired, antimony trioxide may be used as a synergist in concentrations ranging from about 2 pph to about 12 pph.

All parts and percentages herein, unless otherwise expressly stated, are by weight.

We claim:

1. A salt of 5,5-bis-(bromomethyl)-2-hydroxy-2-oxo-1,3,2-dioxaphosphorinane having the structure:

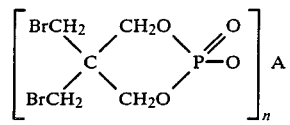

where A is a metal or amine group and n is 1–3.

2. The salt of claim 9 wherein A is aluminum.
3. The salt of claim 9 wherein A is calcium.
4. A salt of 5,5-bis-(bromomethyl)-2-hydroxy-2-oxo-1,3,2-dioxaphosphorinane having the structure:

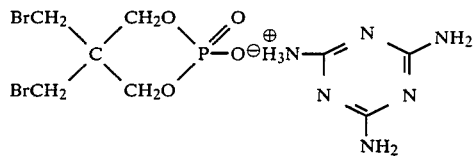

said salt being a solid.

5. The salt of claim 1 wherein A is magnesium.
6. The salt of claim 1 wherein A is zinc.
7. A process for preparing salts of 5,5-bis-(bromomethyl)-2-hydroxy-2-oxo-1,3,2-dioxaphosphorinane comprising reacting (1) 5,5-bis-(bromomethyl)-2-chloro-2-oxo-1,3,2-dioxaphosphorinane with (2) a water-soluble metal salt or an amine, in the presence of water, to form the corresponding salt of 5,5-bis-(bromomethyl)-2-hydroxy-2-oxo-1,3,2-dioxaphosphorinane, and isolating said salt from the process mixture.
8. The process of claim 7 wherein the reactant of (2) is a polyvalent metal halide.
9. The process of claim 7 wherein the reactant of (2) is aluminum chloride.
10. The process of claim 7 wherein the reactant of (2) is calcium chloride.
11. The process of claim 7 wherein the reactor of (2) is an amine.
12. The process of claim 7 wherein the reactant of (2) is an amino-s-triazine.
13. The process of claim 7 wherein the reactant of (2) is melamine.

* * * * *

UNITED STATES PATENT AND TRADEMARK OFFICE
CERTIFICATE OF CORRECTION

PATENT NO. : 4,551,527
DATED : November 5, 1985
INVENTOR(S) : Yuval Halpern et al It is certified that error appears in the above-identified patent and that said Letters Patent is hereby corrected as shown below:

On the title page inventors should read

-- (75) Inventor: Yuval Halpern, Skokie, ILL. --.

*Signed and Sealed this*

*Eighteenth* Day of *February 1986*

[SEAL]

*Attest:*

DONALD J. QUIGG

*Attesting Officer*  *Commissioner of Patents and Trademarks*